(12) United States Patent
Shoemaker et al.

(10) Patent No.: US 9,254,484 B2
(45) Date of Patent: *Feb. 9, 2016

(54) METHODS AND SYSTEMS FOR PROCESSING SAMPLES ON POROUS SUBSTRATES

(71) Applicant: WHATMAN INTERNATIONAL LIMITED, Maidstone (GB)

(72) Inventors: Philip Alexander Shoemaker, Scotia, NY (US); Weston Blaine Griffin, Niskayuna, NY (US); Erin Jean Finehout, Clifton Park, NY (US); Xuefeng Wang, Schenectady, NY (US); Kashan Ali Shaikh, Clifton Park, NY (US); Greg Darryl Goddard, Ballston Spa, NY (US)

(73) Assignee: WHATMAN INTERNATIONAL LIMITED, Maidstone (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/202,222

(22) Filed: Mar. 10, 2014

(65) Prior Publication Data

US 2014/0248714 A1 Sep. 4, 2014

Related U.S. Application Data

(63) Continuation of application No. 12/629,088, filed on Dec. 2, 2009, now Pat. No. 8,685,749.

(51) Int. Cl.
| | |
|---|---|
| *G01N 1/40* | (2006.01) |
| *G01N 1/28* | (2006.01) |
| *B01L 3/00* | (2006.01) |
| *G01N 35/10* | (2006.01) |
| *G01N 1/34* | (2006.01) |
| *G01N 30/72* | (2006.01) |
| *G01N 35/00* | (2006.01) |

(52) U.S. Cl.
CPC .............. *B01L 3/50255* (2013.01); *G01N 1/34* (2013.01); *G01N 1/405* (2013.01); *G01N 35/1095* (2013.01); *B01L 2200/0689* (2013.01); *B01L 2300/0829* (2013.01); *G01N 30/7233* (2013.01); *G01N 2035/00128* (2013.01); *Y10T 436/24* (2015.01); *Y10T 436/25* (2015.01); *Y10T 436/255* (2015.01); *Y10T 436/25375* (2015.01)

(58) Field of Classification Search
CPC .......... G01N 1/405; G01N 1/40; G01N 1/28; G01N 1/00; G01N 1/34; G01N 35/1095; G01N 35/10; G01N 35/00; B01L 3/50255; B01L 3/5025; B01L 3/502; B01L 3/50; B01L 3/00; Y10T 436/00; Y10T 436/24; Y10T 436/25; Y10T 436/11; Y10T 436/112499; Y10T 436/113332

USPC ................ 436/178, 177, 174; 435/29, 287.1; 73/38, 37

See application file for complete search history.

(56) References Cited

U.S. PATENT DOCUMENTS

| | | | |
|---|---|---|---|
| 3,879,127 | A | 4/1975 | Storr et al. |
| 5,460,057 | A | 10/1995 | Ostrup |
| 5,595,653 | A | 1/1997 | Good et al. |
| 5,638,170 | A | 6/1997 | Trinka et al. |
| 5,641,682 | A | 6/1997 | Pagels et al. |
| 5,762,873 | A | 6/1998 | Fanning et al. |
| 6,372,504 | B1 | 4/2002 | Tervamaki et al. |
| 6,592,826 | B1 | 7/2003 | Bloecker et al. |
| 7,217,513 | B2 | 5/2007 | Parameswaran et al. |
| 7,364,914 | B2 | 4/2008 | Buchanan |
| 2002/0051996 | A1 | 5/2002 | Siani et al. |
| 2002/0084214 | A1 | 7/2002 | Astle |
| 2003/0133843 | A1 | 7/2003 | Hilhorst et al. |
| 2004/0101966 | A1 | 5/2004 | Davis et al. |
| 2004/0166554 | A1 | 8/2004 | Chamoles |
| 2005/0129579 | A1 | 6/2005 | Morrison |
| 2005/0208477 | A1 | 9/2005 | Cima et al. |
| 2005/0287678 | A1 | 12/2005 | Morrison |
| 2006/0182657 | A1 | 8/2006 | Pathirana et al. |
| 2006/0252054 | A1 | 11/2006 | Lin et al. |
| 2007/0148649 | A1 | 6/2007 | Shigesada et al. |
| 2009/0117011 | A1 | 5/2009 | Morrison |

(Continued)

FOREIGN PATENT DOCUMENTS

| | | | |
|---|---|---|---|
| EP | 2330402 | A1 | 6/2011 |
| EP | 2507640 | A1 | 10/2012 |

(Continued)

OTHER PUBLICATIONS

PCT Search Report from PCT/EP2010/068457 dated Mar. 21, 2011.

(Continued)

*Primary Examiner* — Christine T Mui
(74) *Attorney, Agent, or Firm* — Fletcher Yoder, P.C.

(57) ABSTRACT

Methods and systems for processing samples fixed to a porous substrate generally comprising, a compressor defining one or more fluid isolation areas, a support, for the porous substrate, having an opening corresponding to one or more of the fluid isolation areas of the compressor, an actuator that causes at least a portion of the compressor to press against the porous substrate, a fluid inlet having access to the fluid isolation area at least when the compressor is pressed against the porous substrate, and a fluid outlet to receive fluid, through the opening in the support corresponding to the fluid isolation area of the compressor, at least when the compressor is pressed against the porous substrate.

22 Claims, 8 Drawing Sheets

(56) References Cited

U.S. PATENT DOCUMENTS

| | | | |
|---|---|---|---|
| 2011/0129863 A1 | 6/2011 | Shoemaker et al. | |
| 2011/0129940 A1 | 6/2011 | Gijlers et al. | |

FOREIGN PATENT DOCUMENTS

| | | | |
|---|---|---|---|
| GB | 1392304 | A | 4/1975 |
| GB | 2477595 | A | 8/2011 |
| GB | 2486946 | A | 7/2012 |
| JP | 564869 | B1 | 2/1981 |
| JP | 6242056 | A | 2/1987 |
| JP | 09192415 | A | 7/1997 |
| JP | 09271397 | A | 10/1997 |
| JP | 2002506386 | A | 2/2002 |
| JP | 2003517591 | A | 5/2003 |
| JP | 2004118877 | A | 4/2004 |
| JP | 2004180637 | A | 7/2004 |
| JP | 2004180637 | A1 | 7/2004 |
| JP | 2005172707 | A | 6/2005 |
| JP | 2009504161 | A | 2/2009 |
| WO | 9820353 | A1 | 5/1998 |
| WO | 0054023 | A | 9/2000 |
| WO | 0054023 | A1 | 9/2000 |
| WO | 0141931 | A2 | 6/2001 |
| WO | 03065037 | A2 | 8/2003 |
| WO | 2007022026 | A2 | 2/2007 |
| WO | 2011067221 | A1 | 6/2011 |

OTHER PUBLICATIONS

PCT Written Opinion from PCT/EP2010/068457 dated Mar. 21, 2011.
G. J. Van Berkel et al., "Application of a Liquid Extraction Based Sealing Surface Sampling Probe for Mass Spectrometric Analysis of Dried Blood spots and Mouse Whole-Body Thin Tissue Sections," Analytical Chemistry, vol. 81, No. 21, Nov. 1, 2009, pp. 9146-9152.
GB Search Report and Written Opinion from Application No. GB1020198.6 dated Apr. 1, 2011.
GB Search Report from Application No. GB1121176.0 dated Apr. 26, 2012.
Examination Report from GB Application No. GB1121176.0 dated Aug. 7, 2013.
Deglon et al., "On-line desorption of dried blood spot: A novel approach for the direct LC/MS analysis of m-whole blood samples", Journal of Pharmaceutical and Biomedical Analysis, vol. 49, No. 4, pp. 1034-1039, Feb. 2009.
Search Report from CN Application No. 201080054714.0 dated Nov. 25, 2013.
Unofficial translation of Japanese Office Action from JP Application No. 2012-541451 on Mar. 4, 2014.
Mar. 31, 2011 Search Report—Application No. GB1020198.6.
Mar. 21, 2011 Search Report—PCT/EP2010/068457.
Mar. 21, 2011 Written Opinion—PCT/EP2010/068457.
Apr. 26, 2012 Search Report—Application No. GB1121176.0.
Aug. 7, 2013 Search Report—Application No. GB1121176.0.
Nov. 25, 2013 Search Report—CN201080054714.0.
Deglon et al., "On-line desorption of dried blood spot: A novel approach for the direct LC/MS analysis of mu-whole blood samples", Journal of Pharmaceutical and Biomedical Analysis, vol. 49, No. 4, pp. 1034-1030, Feb. 2009.
Van Berkel et al., "Application of a Liquid Extraction Based Sealing Surface Sampling Probe for Mass Spectrometric Analysis of Dried Blood Spots and Mouse Whole-Body Thin Tissue Sections," Analytical Chemistry, vol. 81, No. 21, pp. 9146-9152, Nov. 1, 2009.

METHODS AND SYSTEMS FOR PROCESSING SAMPLES ON POROUS SUBSTRATES

CROSS REFERENCE TO RELATED APPLICATIONS

This application is a continuation of U.S. patent application Ser. No. 12/629,088, entitled "Methods and Systems for Processing Samples on Porous Substrates", filed Dec. 2, 2009, which is herein incorporated by reference in its entirety.

BACKGROUND

The invention relates generally to methods and systems for processing samples on porous substrates.

Porous substrates, such as cellulose matrices (e.g. 31 ETF, FTA and FTA elute cards available from Whatman) are often used to store biological samples, such as blood. A new application area for these cards is in the pharmaceutical industry, which is using them to store dried blood samples from pharmacokinetic and toxicokinetic studies. When it is time to analyze the amount of drug or drug metabolite in the dried blood spot, the current methods require the user to cut the sample out of the card, usually a 1-6 mm diameter circle, place the cut disc in a vial or well with extraction fluid, and then shake/vortex for a set period of time. The extraction fluid is then removed and analyzed using a method such as LC-MS.

The pharmaceutical industry is expecting to process a large number of samples per day and is therefore looking for ways to automate the process. The current workflow of disc cutting and extraction, poses several problems when facing the challenge of automation. The primary problems arise from the cutting step. The small cut discs are highly prone to the effects of static electricity or even a light breeze. There are numerous reports of cut discs being lost during the cutting step or during transport of the cut discs. Cross-contamination is another significant problem associated with having to cut pieces out of the FTA cards because small fibers are often released during cutting. These small fibers can then cause cross-contamination between samples.

Previous attempts to automate the workflow include cutting out a portion of the card with sample dried on it. The cut disc is then placed in a vial/well, to which extraction fluid is added, and then shaken/vortexed for a set period of time. Alternatively, the cut disc is placed in a device that allows one to flow fluid through it to extract analytes. All of these approaches suffer from the problems and risks associated with cutting (e.g. lost sample discs, loose fiber contamination, contamination from the cutting blade).

Another approach has been to pre-cut a portion of a blank card, place the sample on the pre-cut disc of substrate, and then extract from the entire disc (by vortexing, shaking, or flow-through). Although this process addresses some of the risks associated with cutting (e.g. the cutting is done before sample application), it has limited application of use and does not allow one to analyze the sample multiple times. The uses of this method are limited because of the dependence of this process on the amount of blood fixed to the card. If the amount of sample applied to the precut disc is not consistent, the amount of drug or drug metabolite will also not be consistent. There are many situations and environments where it is difficult to achieve an accurate and consistent amount of sample collection. Inconsistency may, for example, be due to the manner in which the sample is collected (i.e. fingerstick for blood) or the training level of the people collecting the samples.

Another approach has been to place the card on a hard surface and then press down with a circular knife-edge, which presses against card but does not cut through it. Extraction buffers are then passed over the surface of the card that is isolated by the knife-edge. This method avoids cutting, but does not ensure that the fluid extracts from the full depth of the card (e.g. only the analytes at the surface may be extracted). It also does not provide a way to remove the fluid from the isolated area of the card before removing the knife-edge. This could lead to fluid wicking into the surrounding area after the knife-edge is removed. This would damage the remaining sample making re-sampling from another position on the card difficult or impossible. Also, when flowing fluid over the top of the sample, fibers are sometimes released. This approach also uses an in-line fit to remove released fibers. However, these fits may become clogged overtime and cause cross-contamination and thus must be cleaned or replaced between samples and this requires additional steps from the user.

BRIEF DESCRIPTION

The methods and systems of the invention generally relate to extracting analytes from samples dried onto porous substrates (such as a cellulose card) for analysis of drug and drug metabolites in body fluids. The methods generally use compression to isolate an area of the card through which an extraction buffer is then flowed through, perpendicular to the surface of the card. The method may comprise a clearing step to remove remaining extraction buffer from the card and system. This method overcomes the risks and problems associated with cutting the paper prior to extraction. By flowing the fluid perpendicular to the paper within the compression seal, this ensures that the extraction is uniform across the isolated area. Performing additional extractions from different positions on the blood spot is also possible with these methods. For example, the clearing step ensures the integrity of the sample around the isolated area is maintained when the compression force is removed.

The methods and system also allow easy integration of a disposable membrane to remove any fibers that are released as fluid flows through the cellulose substrate. The membrane may be added and replaced without any additional steps by the user, facilitating the connection of the system directly to an analysis system such as a mass spectrometer.

The methods and systems of the invention overcome several of the challenges in automating the use of cellulose matrix cards such as FTA and FTA Elute. The methods and systems allow one to extract from a defined area of the porous substrate without having to cut. This eliminates the risk of losing a cut disc or creating loose fibers during cutting that could contaminate another sample. It also enables more than one test to be applied to, not only the entire sample on the card, but also to that portion of the sample isolated by compression. The methods and systems result in a consistent quantity of sample being tested, because they effectively isolate a defined area of the sample. For example, even if the amount of blood collected on the paper varies, the methods are always extracting/analyzing the same area of dried blood. For products, such as the Whatman cards, where the sample wicks out uniformly, analyzing the same area is equivalent to analyzing the same volume of the original sample material. Improving the automation solutions available for cellulose card handling supports the growth of these materials in fields such as the pharmaceutical industry which that require high-throughput analysis.

An example embodiment of the system of the invention, for processing samples fixed to a porous substrate, comprises: a compressor defining one or more fluid isolation areas; a support, for the porous substrate, having an opening corresponding to the fluid isolation area of the compressor; an actuator that causes at least a portion of the compressor to press against the porous substrate; a fluid inlet having access to the fluid isolation area at least when the compressor is pressed against the porous substrate; a fluid outlet to receive fluid, through the opening in the support corresponding to the fluid isolation area of the compressor, at least when the compressor is pressed against the porous substrate. The system may further comprise a compressible membrane or filter, to remove fibers. The membrane or filter is placed between the porous substrate and the compressor so that the fluid exiting the porous substrate travels through the membrane or filter before entering the fluid outlet.

The compressor may comprise a top seal plug and a bottom seal plug, one or both of which the actuator causes to press against the porous substrate; wherein the bottom seal plug has an opening in fluid communication with the opening in the support and an opening in fluid communication with the fluid outlet. The top seal plug may have an opening in fluid communication with the fluid inlet. The system may further comprise a receptacle comprising a plate having a plurality of wells and/or vials. The system may also be directly connected to an analysis system such as a mass spectrometer.

Another embodiment of the system, for processing samples fixed to a porous substrate, comprises: a plurality of sample processing subsystems, each of which comprises, a compressor defining one or more fluid isolation areas, a support, for the porous substrate, having an opening corresponding to the fluid isolation area of the compressor, an actuator that causes at least a portion of the compressor to press against the porous substrate, a fluid inlet having access to the fluid isolation area at least when the compressor is pressed against the porous substrate, a fluid outlet to receive fluid, through the opening in the support corresponding to the fluid isolation area of the compressor, at least when the compressor is pressed against the porous substrate; a manifold in fluid communication with the fluid inlet of the sample processing subsystems; a cassette for housing a plurality of porous substrates: a receptacle shuttle subsystem for transporting one or more fluid receptacles to the sample processing subsystems; an automated assembly for transporting the porous substrates from the cassette to the sample processing subsystems; and a controller that coordinates the sample processing subsystems and the automated assembly. The system may further comprise an imaging subsystem for imaging the substrates to identify the location of the sample on the porous substrates. The automated assembly may comprise a robotic subassembly and a guide along which the robotic subassembly moves between the cassette and the sample processing systems. The automated assembly also transports the porous substrates to the imaging subsystem.

Another embodiment of the system, for processing samples fixed to a porous substrate, comprises: a compressor defining one or more fluid isolation areas; a support for the porous substrate, having an opening corresponding to the fluid isolation area of the compressor; an actuator that causes at least a portion of the compressor to press against the porous substrate; a fluid inlet having access to the fluid isolation area at least when the compressor is pressed against, the porous substrate; a fluid outlet to receive fluid, through the opening in the support corresponding to the fluid isolation area of the compressor, at least when the compressor is pressed against the porous substrate; and a clearing component that cleans one or more of the opening in the support, the fluid inlet, or the fluid outlet. The clearing component may clear, for example, by forcing a gas through one or more of the openings in the support, the fluid inlet, or the fluid outlet.

An example of the method for processing samples fixed to a porous substrate on a support may comprise: creating a compression seal, on the porous substrate, to form an isolation zone within which a portion of the sample is thereby isolated; applying a fluid to the sample isolated in the isolation zone by flowing the fluid through the isolated zone; collecting at least a portion of the fluid after it is flowed through the isolation zone; clearing the fluid from the isolation zone by flowing gas through the isolated zone; releasing the compression seal; and analyzing one or bath of the collected fluid and the portion of the sample in the isolation zone. The method may further comprise imaging the sample on the porous substrate before creating the compression seal, and/or imaging the sample after the fluid is collected. The step of creating the compression seal may also comprise compressing a compressible membrane of filter along with the porous substrate. The analyzing step may comprise quantifying an amount of one or more substances in the collected fluid. In methods in which the sample comprises blood or other various types of biological materials, the analyzing step may comprise identifying one or more components of the sample. The step of creating the compression seal may comprise forming a plurality of isolation zones on the porous substrate. A plurality of fluids may be applied to the sample simultaneously or serially.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The methods, devices and systems of the invention generally compress an area of a porous substrate, such as a cellulose card, to isolate a portion of the substrate on which a biological sample has previously been placed, and then pass an extraction buffer through the isolated portion of the substrate, perpendicular to the plane of the substrate, to extract at least a portion of the biological sample from the card.

Another embodiment of the system for processing samples fixed to a porous substrate comprises: a compressor defining one or more fluid isolation areas; a support, for the porous substrate, having an opening corresponding to the fluid isolation area of the compressor; an actuator that causes at least a portion of the compressor to press against the porous substrate; a fluid inlet having access to the fluid isolation area at least when the compressor is pressed against the porous substrate; a fluid outlet to receive fluid, through the opening in the support corresponding to the fluid isolation area of the compressor, at least when the compressor is pressed against the porous substrate; and a clearing component that clears one or more of the opening in the support, the fluid inlet or the fluid outlet. The clearing component may clear, for example, by forcing a gas or a liquid through one or more of the opening in the support, the fluid inlet or the fluid outlet.

Following are non-limiting examples used to illustrate various examples and embodiments of the methods and systems for processing samples on porous substrates.

EXAMPLE

Figure 1:
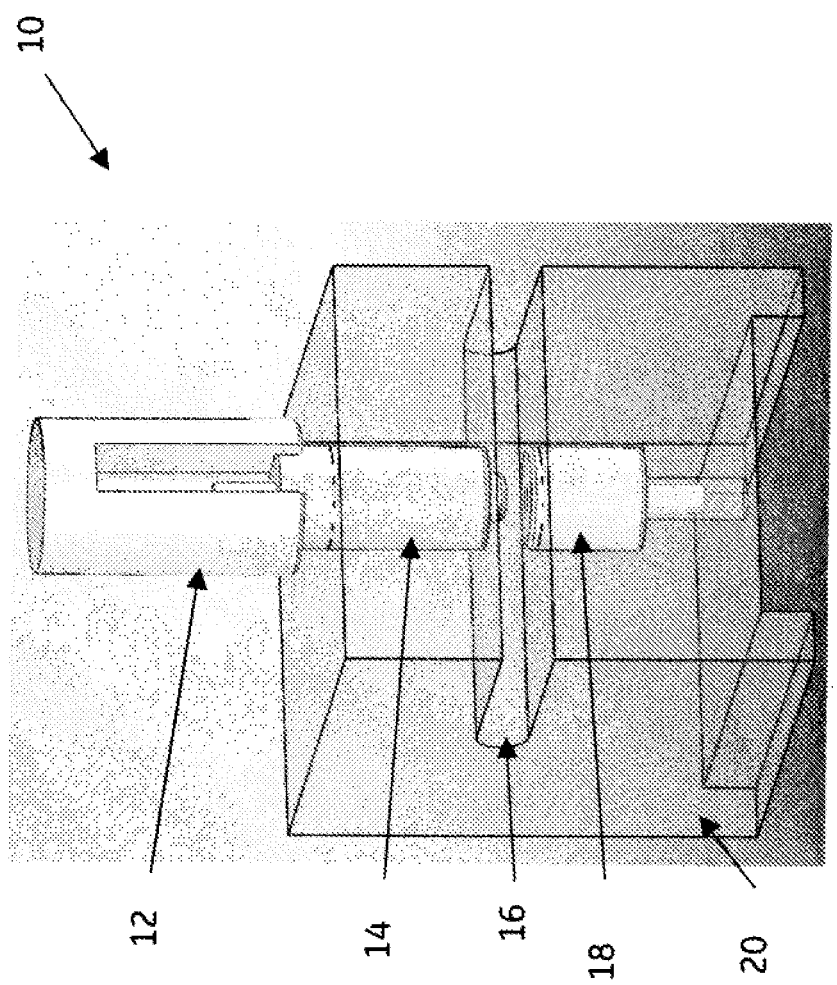
FIG. 1 is a perspective drawing of an embodiment of a compressor of the invention for processing samples on a porous substrate.
Figure 2:
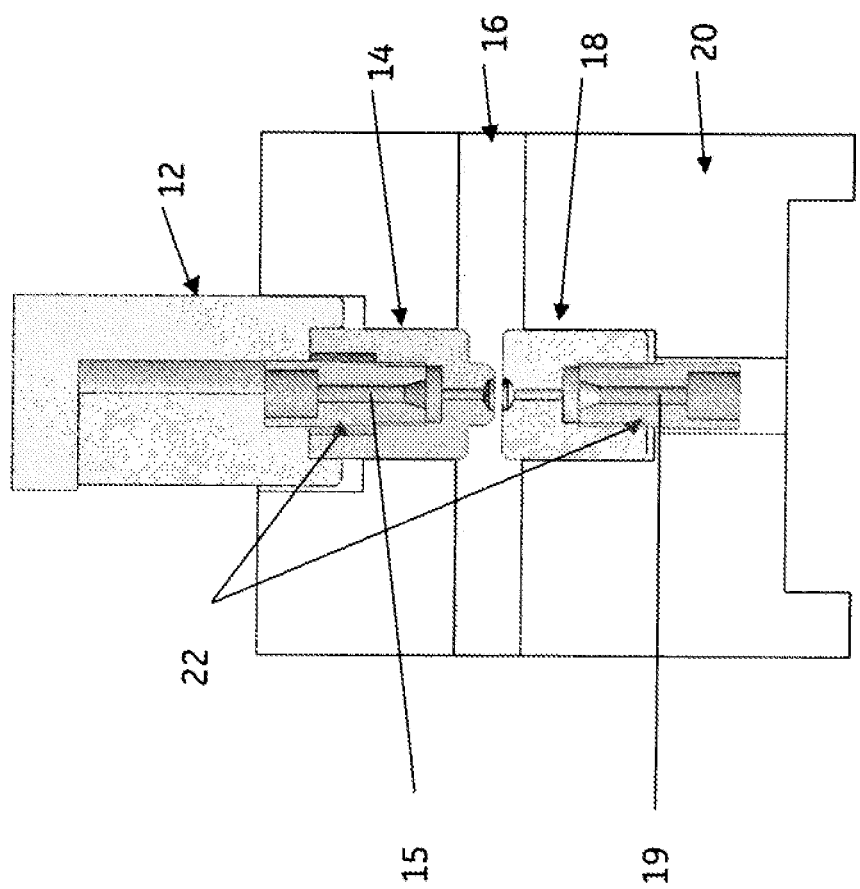
FIG. 2 is a cross-sectional drawing of the embodiment of the compressor shown in FIG. 1.
Figure 3:
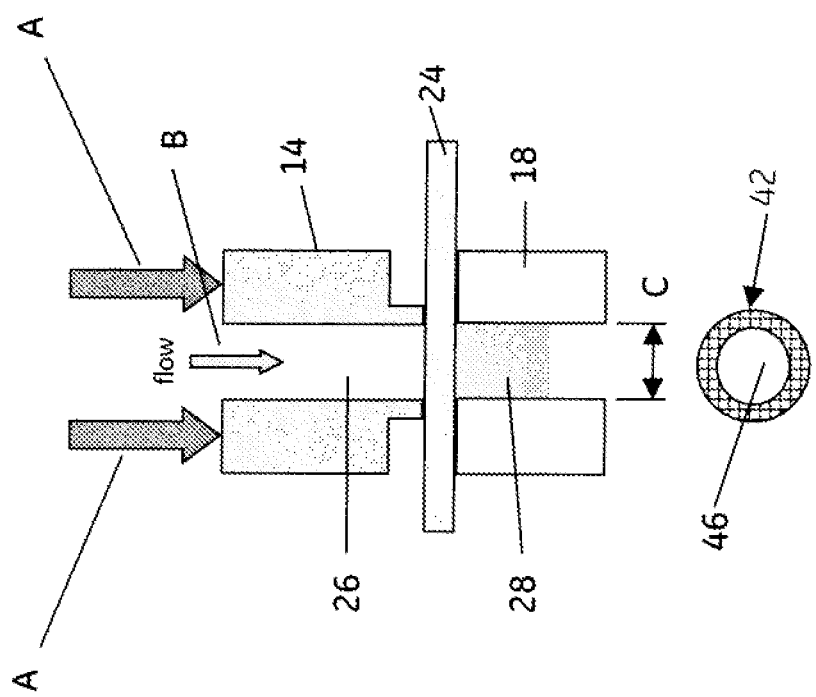
FIG. 3 is a schematic drawing of an example of the method of the invention using the compressor shown in FIG. 1.

As shown in FIGS. 1-3, an embodiment of a compression device, generally referred to as device 10, of the invention comprises, a compressor which may comprise, for example, the top seal plug 14 and the bottom seal plug 18, wherein the top and bottom plugs have a fluid inlet and fluid outlet, respectively, or channels 15 and 19, with openings that define an isolation area, that allow for the passage of fluid. The channels of the plugs of this example are matched in size and aligned so that, if the top and bottom plug were in contact with each other, fluid would flow through the two parts without obstruction. In this non-limiting embodiment, the flow through the channels has a circular cross section with a 3 mm diameter at the parting line, isolation area, of the two parts. The channel may narrow, as shown, for example in FIG. 2, in cross section above and below the parting line of the two parts. The hollow plugs at the parting line, in this non-limiting example, have a sealing area 42 of 0.0139 in$^2$ (9 mm$^2$) to form an isolation area 46 with a 3 mm diameter cross section. A flangeless tubing nuts 22 (ferrule not shown) is used in this example to support tubing, having an outside diameter of 1/16" and an inside diameter of 1 mm, to transport fluid, such as a buffer through the fluid inlet 26 and outlet 28. The isolation area 46 is not limited to 3 mm (arrow C) or to a circular cross section. The size and shape of the isolation area may be varied depending on a given application or use of the device.

The top seal plug may be a separate and optionally disposable component that is attached directly to the compression actuator or to an actuator subassembly. The bottom seal plug may be a separate and possibly disposable component that is accurately positioned by the base support structure. Alternatively, the bottom seal plug could be an integral part of the base support structure.

To use the device, a porous substrate 24, e.g. a cellulose substrate, is inserted between the top seal plug 14 and bottom seal plug 18 into slot 16. The top seal plug is associated with an actuator, such as top pusher 12, that moves vertically in this example, or generally perpendicular to the surface of the cellulose substrate. The actuator applies a sealing force (shown by arrows A) to the top seal plug relative to the bottom seal plug. The force creates a defined pressure over the area defined by the areas of the two parts that are in common at the parting line, referred to herein as the sealing area 42 that defines isolation area 46. The components of the device are seated in a support base 20. When significant pressure is applied to the sealing area, the fibers of the cellulose substrate compress and significantly limit the flow parallel on the substrate (wicking) to within the isolation area 46, thus effectively directing any fluid flow through, and generally perpendicular to, the paper (as shown by arrow B).

The top and bottom seal plugs effectively press against the porous substrate (e.g. a cellulose card) to create a barrier of compressed fibers that prevent wicking. Without the barrier of compressed fibers, the majority of the fluid would wick outward and along the surface of the paper, rather than flowing perpendicular to it. The isolation area, formed by the compression, allows the system to sample from a defined area without the need to cut and capture pieces of the substrate on which the sample is fixed. For example, there is no need for a step to cut pieces (e.g., discs) of the porous substrate, on which a portion of the sample is fixed, and then a step to capture the cut piece in a receptacle, such as a well. By isolating the fluid path, the methods and systems of the invention eliminate the problems associated with losing the cut pieces and cross-contamination caused by fibers that come loose during the cutting and capturing of the cut pieces. To further avoid contamination between samples, the methods and systems may comprise a wash step between analyte extractions, or may use a disposable cover that is changed between samples (e.g. similar to automated methods and systems that use disposable pipette tips).

Figure 4A:
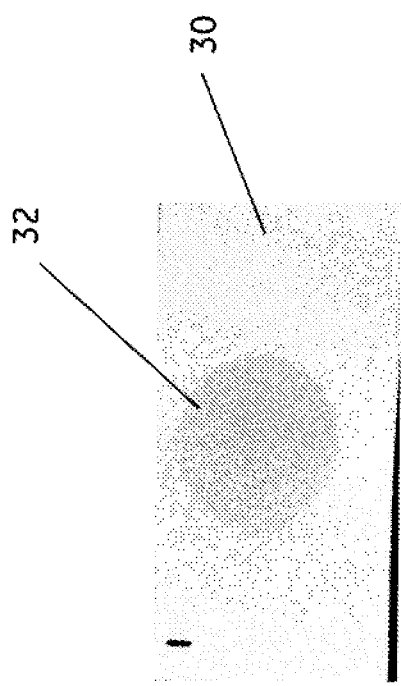
FIG. 4A is an image showing wicking of fluid on a porous substrate without the use of a compressor of the invention.
Figure 4B:
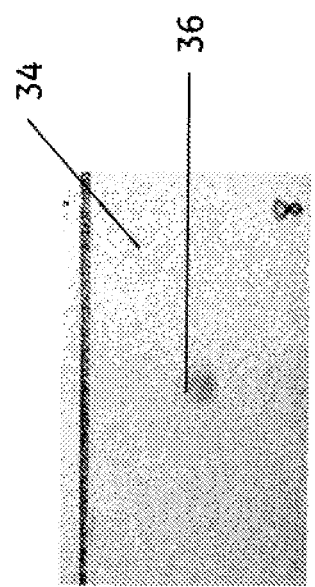
FIG. 4B is an image showing the isolation of fluid within an isolation area using a compressor of the invention.

FIGS. 4A and 4B illustrate the difference between applying a buffer to a porous substrate without compression and with compression, respectively. Specifically, in the example shown in 4A, 50 µL of water (with added food coloring) was applied to and allowed to flow through 31 Et chromatography paper 30 without any compression applied to the pusher head. As shown, the fluid only wicked outward along paper, as shown by spot 32, and does not flow through paper. In contrast, in the example shown in 4B, 50 uL of water (with added food coloring) was applied to and allowed to flow through 31 Et chromatography paper 34 with 200 lbf of compression is applied to the pusher head. As shown, the fluid did not wick outside of the isolation area 36. Instead the fluid flowed through, and perpendicular to, the paper and within the boundary of the isolation area.

Figure 5B:
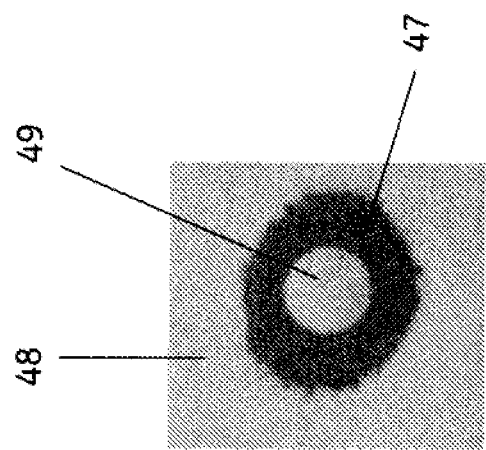
FIGS. 5A and 5B are images of the top and bottom, respectively, of a sample on a porous substrate showing an area on the sample that has been isolated using a compressor of the invention.
Figure 5A:
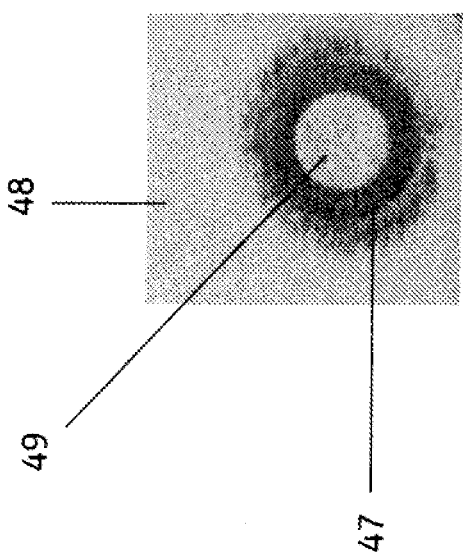

FIGS. 5A and 5B illustrate the effect of using the compression to isolate a sample, showing a top view and a bottom view, respectively, of a porous substrate 48 (e.g. FTA card) after an example of the method is applied to a dried blood sample on the substrate. In this example, water was applied and allowed to flow through a 3 mm isolation area 49, generally determined by the shape and size of the compression area 47, of a dried blood spot. As shown, the water removed the hemoglobin from the spot, as shown by the white, round area of isolation area 49. The area of extraction is uniform when view from the top (FIG. 5A) or the bottom (FIG. 5B) of the porous substrate.

Example

An example of one of the methods of the invention for processing samples on a porous substrate comprises, placing a porous substrate (containing dried analyte) in the slot of the device so that heads of the seal plugs are aligned with the desired extraction area, then applying a force to seal plugs (via pusher). The heads of the seal plugs compress the paper forming a seal which prevents liquids, such as an extraction buffer, that are introduced to the isolation area, via a fluid inlet, from wicking outward from the initial point at which the buffer is applied to the substrate. The buffer is applied to the substrate through an inlet tube that located, in this example, within a hollow bore concentrically located in the first pusher. The buffer that flows through the paper, without wicking outside the isolation area, and then through an outlet tube that is located, in this example, within a hollow bore concentrically located in the bottom, or second, pusher, and into a receptacle such as a well plate or a vial. One or both of the pushers (seal plugs) may move towards the other or one may be stationary and while only the other pusher move towards the stationary pusher. The fluid in this example flows in a direction that is perpendicular to the paper. After one or more extractions, the surfaces of the device that come into contact with the sample and/or the extraction fluids may be cleaned or otherwise cleared of materials to reduce or prevent cross contamination. For example, air may be introduced into and forced through, the device or system to remove any remaining liquid or foreign materials within the fluid path, while the compression force is being applied. Air may also be introduced to remove excess fluid from the sample area to dry the location and prevent wicking of fluids after the compression force is released. Then the compression force is released from the seal plugs and the paper is removed from the slot. The clearing step may also be carried out, or repeated, after the paper is removed and the compression forced reapplied to reconnect the fluid path through the various components of the device or system.

Figure 6:
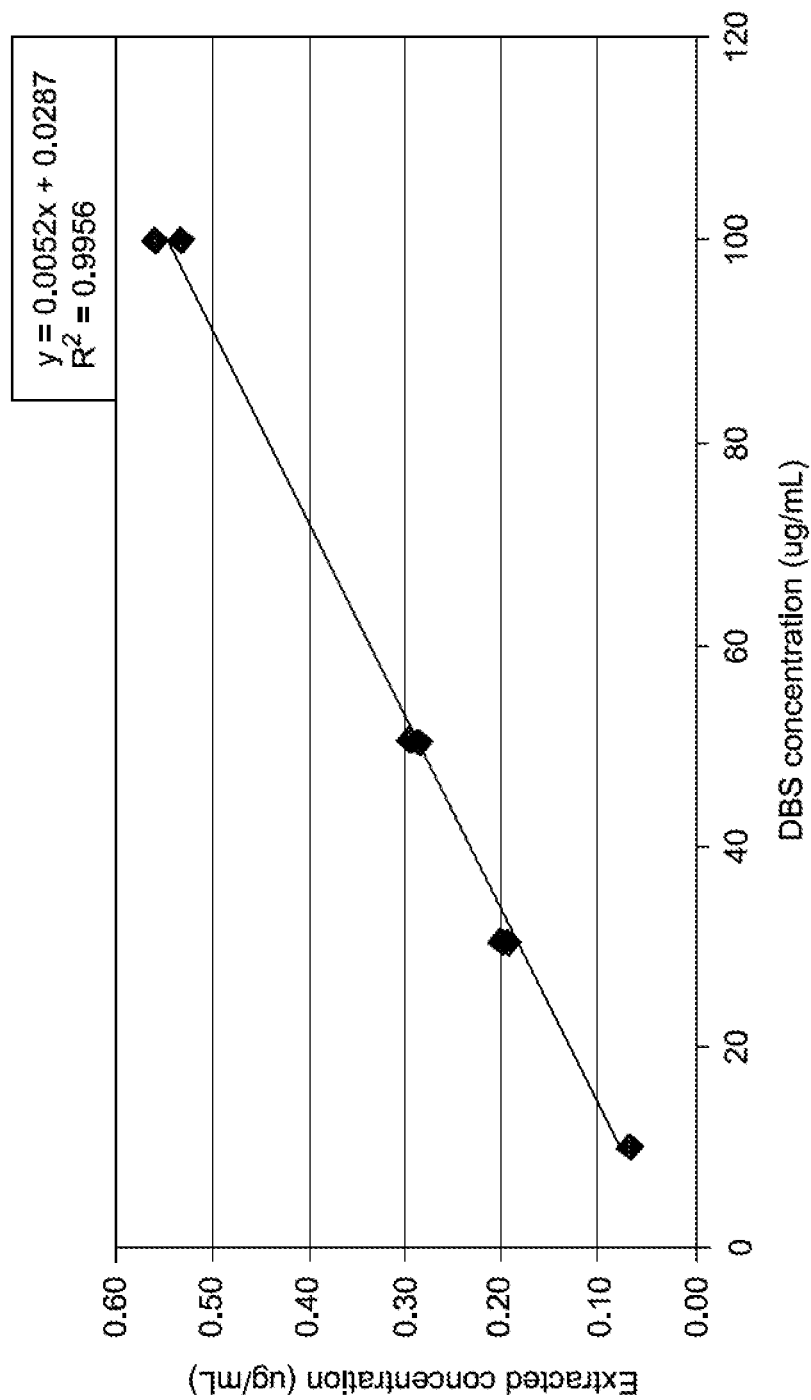
FIG. 6 is a plot showing the amount of Hyamine extracted from dried blood spots spiked with varying amounts of Hyamine.

As a more specific, but non-limiting, example, blood samples were treated with varying amounts of Hyamine and then 15 ul of the blood sample was applied to an FTA card. A portion of the blood spot was isolated, by applying compression around a portion of the blood sample. Then 300 ul of 70% THF was introduced through the fluid inlet and allowed to flow through the blood spot within the isolation area bounded by the compression area (e.g. 3 min inner diameter) at 60 ul/min. The 70% THF is collected in a vial after exiting the outlet and is then analyzed using liquid chromatography-mass spectrometry (LC-MS) and calibration standards are used to convert peak intensity reading into concentration data. FIG. 6 shows a plot of the concentration of Hyamine extracted from each of the blood spots. There is a linear correlation between the amount of drug spiked into the blood and the amount extracted.

The methods and systems of the invention may analyze the samples and materials extracted from the samples for many different purposes using a variety of analyzing systems such as, but not limited to, immunoassays (e.g. to identify the presence or absence of a component), liquid chromatography with UV detection (e.g. to characterize and quantify components), and liquid chromatography with mass spectrometry (e.g. to identify and/or quantify components).

As another more specific, but non-limiting, example. Proguanil was spiked into a blood sample at 50 ug/mL and 15 uL aliquots of the blood were applied to an FTA card. A compressible membrane (Pall Life Sciences Supor-200 membrane filter, 0.2 um pore) was placed between an FTA card with the dried sample 24 and the bottom seal plug 18. Fluid leaving the isolated area must pass through the membrane before going through the outlet. The pore size of the membrane is smaller than any fibers that may be released. The card and membrane are both compressed in the device. Extractions were performed using the compression system with 100 uL of 70% THF. The 70% THF is collected in a vial after exiting the outlet and is then analyzed using liquid chromatography-mass spectrometry (LC-MS) and calibration standards are used to convert peak intensity reading into concentration data. Two replicates were performed. Below is a table illustrating the amount of drug detected in the extraction buffer with and without the membrane. Adding the membrane did not decrease the isolation integrity or extraction efficiency.

| With Membrane | Without Membrane |
|---|---|
| 0.29 ug/mL, 0.31 ug/mL | 0.28 ug/mL, 0.29 ug/mL |

Figure 7:
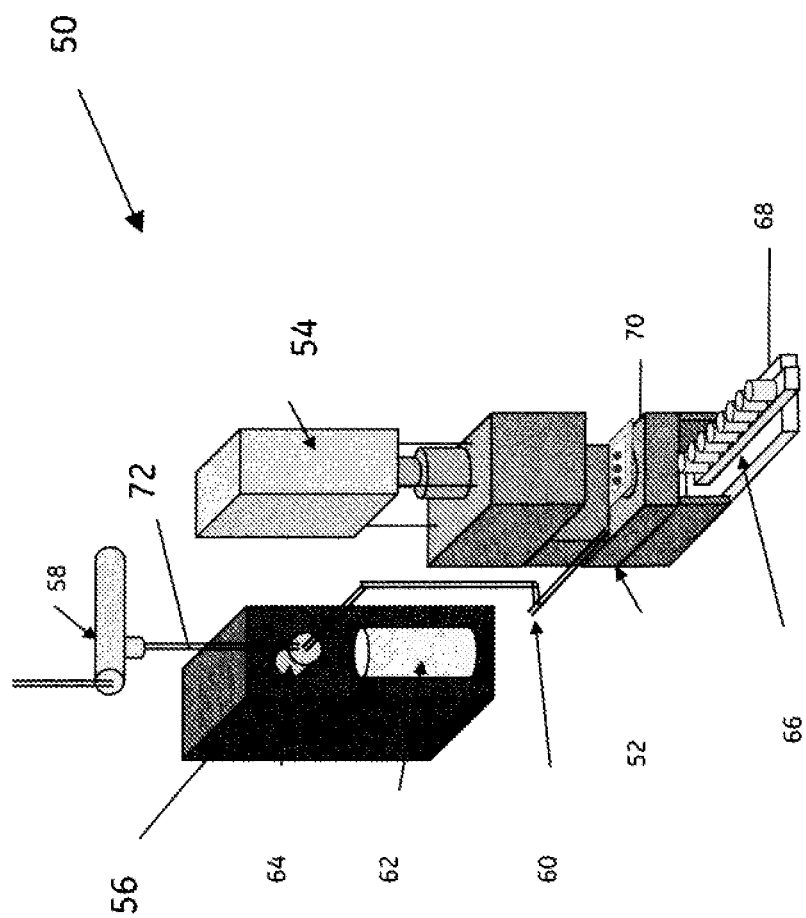
FIG. 7 is a perspective drawing of an embodiment of a compressor unit and a fluid unit of the invention for processing samples on a porous substrate.

The methods and systems may be adapted for high-throughput applications. FIG. 7 is an example embodiment of a high-throughput compression device 50 for processing samples on porous substrates 70. The device of this embodiment comprises a compression unit 52, a pusher 54, and a vial strip 66 on which a plurality of vials 68 are positioned. The system further comprises a fluidic unit 56, for introducing fluidic materials such as an extraction buffer, which is in fluid communication with the compression unit 52 via a fluid path 60. The fluidic device comprises a syringe pump 62, a multi-port valve 64 and a solvent manifold 58. The device may be a stand-alone device or it may be one of several such devices in a larger processing system as shown in FIG. 8.

Figure 8:
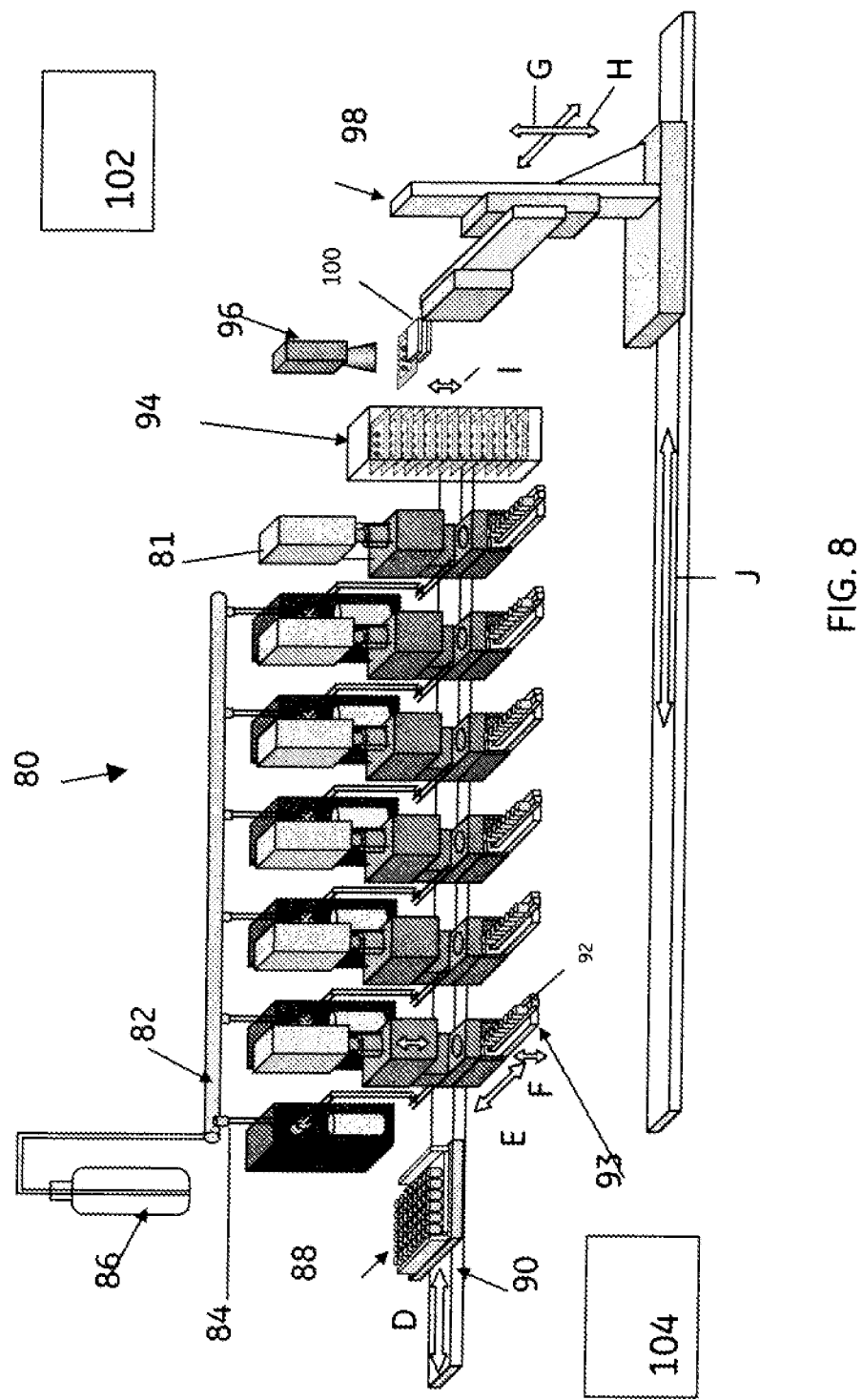
FIG. 8 is a perspective drawing of an embodiment of a high throughput system of the invention for processing samples on a porous substrate.

The embodiment of the high-throughput system 80 shown in FIG. 8 generally comprises a plurality (e.g. two or more) of compression devices 81, comprising for example, the compression unit 52 shown in FIG. 7, in fluidic communication with one or more fluidic devices 56. The solvent manifold 82 may be a single manifold, as shown, that supplies solvent from a solvent tank 86 to the fluidic devices via connectors 84 in parallel, or may comprise multiple manifolds each associated with one or more of the fluidic devices and/or supplying differing materials to the fluidic devices. The system may comprise well plate shuttles 88 for transporting vial strips along a linear slide or conveyor 90 from a well-plate stacking device 104 to a plurality of compression devices 81 in the direction shown by arrow D. Each of the compression devices may comprise a vial strip shuttle 92 and a vertical action, linear slide 93 to maneuver vial strips on and of the well plate shuttle 88, and into a fluidic extraction path of a given compression device, as shown by arrows E and F. The vials in the vial strips may comprise pierceable caps for transferring the materials extracted from the sample spots into the vials. The pierceable caps may be made of materials that self-repair after piercing to maintain the integrity of the materials in the vials.

In the embodiment of a high-throughput system shown in FIG. 8, the system is an asynchronous parallel processing system that comprises a multi-axis (e.g. three-axes illustrated, for example, by arrows G, H and J) Cartesian robot 98, with a gripper 100, that maneuvers the FTA cards from a magazine cassette 94, used to support and/or handle multiple FTA cards, to the compression devices. The robot may also be used to maneuver the FTA cards to one or more imaging position/locations associated with an imaging device 96 (e.g. digital camera) so that an image can be taken of the FTA card after (and/or before) one or more materials are extracted from one or more samples on the FTA cards. The images may then be processed to analyze the imaged sample spots on the FTA cards using a detection system (not shown). A controller 102 may be programmed to coordinate the various subsystems and devices of system 80, including coordination of the plurality of sample processing subsystems, each of which, in this example embodiment, comprises, a compressor defining one or more fluid isolation areas, a support, for the porous substrate, having an opening corresponding to the fluid isolation area of the compressor, an actuator that causes at least a portion of the compressor to press against the porous substrate, a find inlet having access to the fluid isolation area at least when the compressor is pressed against the porous substrate, a fluid outlet to receive fluid, through the opening in the support corresponding to the fluid isolation area of the compressor, at least when the compressor is pressed against the porous substrate. The controller may also coordinate the timing and introduction of the fluids, such as extraction buffers, via the manifold 82 in fluid communication with the fluid inlets of the sample processing subsystems 81; the movements of automated assembly (e.g. robot 98) for transporting the porous substrates from cassette 94 to the sample processing subsystems 81; the movements of the receptacle shuttle subsystem for transporting one or more fluid receptacles (e.g. vials or well plates) transported on shuttle 88 along linear slide 90 to the sample processing subsystems; and the positioning of each receptacle, on strip shuttle 93 into the fluid path of each sample processing subsystem 81.

Example

A non-limiting example of a process used in connection with system, such as for example the system shown in FIG. 8, variably may comprise the following actions. A well plate is transferred from a plate stacker. A vial strip is retrieved from the well plate shuttle and a vial on the vial strip is positioned in the fluid path of sample processing, subsystem (e.g. 81). The automated assembly (e.g. 98) retrieves an FTA card from the magazine cassette and moves the FTA card into the imaging field of a camera. The imaging system determines the location of one or more samples on the FTA card. The automated assembly then positions the FTA card within the isolation area and fluid flow path of the compression device. The actuator of the compression device is extended to compress the FTA paper. One of the vials is raised to pierce the cover of the vial. Solvent is then pumped from the manifold through the fluid inlet of the compression device and through isolation area of the sample on the FTA card and, together with the extracted materials from the sample, into the receptacle vial. There may be multiple automated assemblies in the same system.

The vial is lowered or otherwise placed back in its position on the receptacle shuttle. A waste line is positioned in the fluid outlet path. Air is pumped through the FTA paper to clear the lines. The compression ram is retracted and the FTA card is removed from the flow through device loaded back into magazine cassette. The FTA card may be imaged by the imaging system before it is placed into the cassette.

A clean FTA card (Or clean portion of a previously sampled card) may then be positioned within the isolation area and fluid flow path of the flow through device to allow cleaning of the system. The rain is extended to compress FTA paper and solvent is pumped through the clean paper while the pressure is modulated to allow for controlled wicking/parallel surface cleaning. Air is again pumped though the lines and paper to clear the lines. The compression ram is retracted and the clean paper card is removed from flow through device. This process may be repeated as needed depending on the capacity of the system. For example, the process is repeated based on a certain number of samples (e.g. 12 samples) on a vial strip, which is then returned to a strip shuttle, or based a certain number of samples on a well plate (e.g. 96 samples), which is then returned to plate-stacker.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for processing samples fixed to a porous substrate comprising,
    a compressor comprising a first portion and a second portion and defining a fluid isolation area when the first portion and the second portion are actuated against a porous substrate;
    a support having an opening corresponding to one or more of the fluid isolation areas of the compressor;
    an actuator that actuates the compressor to move one or both of the first and second portions to isolate only a portion of the porous substrate in the fluid isolation areas;
    a fluid inlet in the first portion in fluid communication with the fluid isolation area; and
    a fluid outlet in the second portion in fluid communication with the fluid isolation area to receive fluid from the fluid isolation area of the compressor, at least when the compressor is pressed against the porous substrate.

2. The system of claim 1, comprising a receptacle comprising a plate having a plurality of wells.

3. The system of claim 1, comprising a receptacle comprising one or more vials.

4. The system of claim 1, further comprising an analysis system.

5. The system of claim 4, wherein the analysis system comprises a liquid chromatography system.

6. The system of claim 4, wherein the analysis system comprises a mass spectrometry system.

7. The system of claim 1, wherein the compressor is configured to form a plurality of fluid isolation areas on the porous substrate.

8. The system of claim 7, wherein the system is configured to collect a plurality of fluid samples from the porous substrate in parallel.

9. A method for processing samples fixed to a porous substrate on a support comprising,
    creating a compression seal around only a portion of the porous substrate, to form an isolation zone within which a portion of the sample is thereby isolated;
    applying a fluid to the sample isolated in the isolation zone to move the fluid through the sample, wherein applying the fluid comprises applying the fluid to a surface of the porous substrate in the isolation zone;
    collecting at least a portion of the fluid after it is applied to the isolation zone;
    analyzing the collected fluid or the portion of the sample in the isolation zone; and
    removing the compression seal from the portion of the porous substrate.

10. The method of claim 9, wherein the porous substrate is disposed in a well.

11. The method of claim 9, comprising applying air to the isolation zone to dry the porous substrate after applying the fluid.

12. The method of claim 9, wherein the collecting comprises collecting the fluid in a vial.

13. The method of claim 9, wherein the analyzing comprises liquid chromatography.

14. The method of claim 9, wherein the analyzing comprises mass spectrometry.

15. A system for processing samples fixed to a porous substrate comprising,
    a plurality of sample processing subsystems, each of which comprises,
        a compressor defining one or more fluid isolation areas;

a support, for the porous substrate, having an opening corresponding to the fluid isolation area of the compressor;

an actuator coupled to the compressor and that, when actuated, causes at least a portion of the compressor to press against the porous substrate to form a compressed fiber barrier against a second portion of the porous substrate that is outside the fluid isolation area;

a fluid inlet having access to the fluid isolation area at least when the compressor is pressed against the porous substrate; and a fluid outlet to receive fluid, through the opening in the support corresponding to the fluid isolation area of the compressor, at least when the compressor is pressed against the porous substrate.

16. The system of claim 15, wherein the plurality of fluid processing subsystems are arranged in series such that the porous substrate passes through each subsystem.

17. The system of claim 15, wherein plurality of fluid processing subsystems are arranged in parallel to analyze a respective plurality of porous substrates.

18. The system of claim 15, comprising a manifold coupled to the fluid inlets of the plurality of fluid processing subsystems.

19. The system of claim 18, comprising a reservoir coupled to the manifold.

20. The system of claim 18, wherein the respective fluid inlets are fluidically coupled to different reservoirs comprising different materials.

21. The method of claim 9, creating a second compression seal around only a second portion of the porous substrate after the compression seal is removed.

22. The method of claim 9, creating a second compression seal around a portion of a second porous substrate after the compression seal is removed.

* * * * *